United States Patent

Yonezawa (10) Patent No.: US 9,420,951 B2
(45) Date of Patent: Aug. 23, 2016

(54) IMAGE PROCESSING APPARATUS AND METHOD OF CONTROLLING SAME

(71) Applicant: CANON KABUSHIKI KAISHA, Tokyo (JP)

(72) Inventor: Keiko Yonezawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 218 days.

(21) Appl. No.: 14/137,396

(22) Filed: Dec. 20, 2013

(65) Prior Publication Data

US 2014/0185007 A1 Jul. 3, 2014

(30) Foreign Application Priority Data

Dec. 28, 2012 (JP) ................................ 2012-287254

(51) Int. Cl.
*A61B 3/14* (2006.01)
*A61B 3/12* (2006.01)
*A61B 3/10* (2006.01)

(52) U.S. Cl.
CPC ............... *A61B 3/12* (2013.01); *A61B 3/1025* (2013.01); *A61B 3/14* (2013.01)

(58) Field of Classification Search
USPC ....... 351/200, 205, 206, 208, 209, 221, 222, 351/223, 243, 244, 245, 246
See application file for complete search history.

(56) References Cited

FOREIGN PATENT DOCUMENTS

| JP | 2008-29732 | * | 2/2008 | ............... A61B 3/14 |
|----|-----------|---|--------|-------------------------|
| JP | 2008029732 A | | 2/2008 | |
| JP | 2010220771 A | | 10/2010 | |
| JP | 2011-98221 | * | 2/2011 | ............... A61B 3/10 |
| JP | 2012016620 A | | 1/2012 | |

OTHER PUBLICATIONS

Vogel, et al., "Retinal motion estimation in adaptive optics scanning laser ophthalmoscopy", Optics Express, Jan. 23, 2006, pp. 487-497, vol. 14, No. 2.

* cited by examiner

*Primary Examiner* — Stephone B Allen
*Assistant Examiner* — Brandi Thomas
(74) *Attorney, Agent, or Firm* — Canon U.S.A. Inc., IP Division (57) ABSTRACT

An ophthalmological apparatus includes a first acquiring unit configured to acquire a first eye fundus image of an eye to be examined on basis of return light from the eye to be examined having a corrected aberration of the eye to be examined, a second acquiring unit configured to acquire a second eye fundus image of the eye to be examined, an aligning unit configured to align the first eye fundus image and the second eye fundus image, and a region setting unit configured to set a candidate region of interest on basis of the alignment.

13 Claims, 11 Drawing Sheets

IMAGE PROCESSING APPARATUS AND METHOD OF CONTROLLING SAME

BACKGROUND OF THE INVENTION

1. Field of the Invention

The present invention relates to ophthalmological apparatuses.

2. Description of the Related Art

For the purpose of early diagnoses of lifestyle-related diseases and high-ranked diseases causing blindness, eye fundus examinations have been widely performed. A scanning laser ophthalmoscope (SLO) that is an ophthalmological apparatus based on the principle of confocal laser scanning microscopy performs raster scanning of laser which is measurement light onto an eye fundus to quickly acquire a high resolution planar image from the intensity of its return light. In recent years, an adaptive Optics SLO (AO-SLO) has been developed which has an adaptive optical system configured to measure in real time the aberration of an eye to be examined with a wave-front sensor and correct the aberration of measurement light or its return light occurring in the eye to be examined with a wavefront correction device and thus allows acquisition of a planar image having high traverse resolution. Moreover, it has been attempted that an image of cones in the retina is extracted by using the acquired planar image of the retina, and its density or distribution is analyzed for disease diagnosis or drug response assessment.

Assessment of the advancement of a disease or changes of cones due to a drug response may require serial observation of an acquired AO-SLO image. Japanese Patent Laid-Open No. 2012-16620 discloses means for performing alignment in a depth direction to compare tomographic images of an eye fundus acquired over time. Japanese Patent Laid-Open No. 2010-220771 discloses a display method which juxtaposes tomographic images and eye fundus images acquired over time and shows a correspondence relationship. Japanese Patent Laid-Open No. 2008-29732 discloses a display method which presents a lesion position detected on an eye fundus image acquired earlier on an eye fundus image acquired subsequently of eye fundus images acquired over time.

Comparison of cones on temporally sequential AO-SLO images may require a comparison of changes in density or turbulences of an alignment state of cones which are handled as a group. For that, the region of interest for comparison must have an identical shape at an identical position on AO-SLO images acquired over time. When a plurality of AO-SLO images are acquired over time, a region of interest may be selected from regions included in all of the acquired AO-SLO images or an AO-SLO image partially not including a selected region is excluded from the comparison subjects. This processing, however, has a problem that an AO-SLO image to be compared with the selected region of interest may not be identified easily. This problem of such temporal comparisons has not been pointed out in the prior arts.

SUMMARY OF THE INVENTION

According to an aspect of the present invention, there is provided an ophthalmological apparatus including a first acquiring unit configured to acquire a first eye fundus image of an eye to be examined on basis of return light from the eye to be examined having a corrected aberration of the eye to be examined, a second acquiring unit configured to acquire a second eye fundus image of the eye to be examined, an aligning unit configured to align the first eye fundus image and the second eye fundus image, and a region setting unit configured to set a candidate region of interest on basis of the alignment.

According to another aspect of the present invention, there is provided a method of controlling an ophthalmological apparatus for imaging a fundus of an eye, the method including a first acquiring step to acquire a first eye fundus image of an eye to be examined on basis of return light from the eye to be examined having a corrected aberration of the eye to be examined, a second acquiring step to acquire a second eye fundus image of the eye to be examined, an aligning step to align the first eye fundus image and the second eye fundus image, and a region setting step to set a candidate region of interest on basis of the alignment.

Further features of the present invention will become apparent from the following description of exemplary embodiments with reference to the attached drawings.

DESCRIPTION OF THE EMBODIMENTS

According to an embodiment, processing will be described which acquires images of the retina captured by an adaptive optical SLO over time and presents a change of an index such as a cone density.

More specifically, the processing acquires an image group as a result of a plurality of examinations including imaging a plurality of points around a macula lutea every several months. Here, imaging one point results in acquisition of a plurality of images with a designated imaging time and frame rate. An image group acquired by imaging one point will sometimes be called "AO-SLO images". In this case, because AO-SLO images may be resulted from imaging of varied ranges, which may provide AO-SLO images having different resolutions. AO-SLO images acquired by imaging a plurality of points and having different resolutions about one eye to be examined will sometimes be called a "Study" collectively for the eye to be examined.

For a temporal observation, an AO-SLO image of interest is selected from a plurality of AO-SLO images included in one Study, images captured at the same fixation position and at different times with those of the AO-SLO image are aligned and presented. Because AO-SLO images captured even at a same fixation position have a displacement due to an influence such as a slight fixation movement, an alignment is performed thereon for correcting such a displacement. A region of interest is selected from an area where images are superimposed as a result. A cone analysis may be performed on each of the images, and analysis results with respect to the selected region may be compared for a temporal assessment.

Configuration of Image Processing Apparatus

Figure 1:
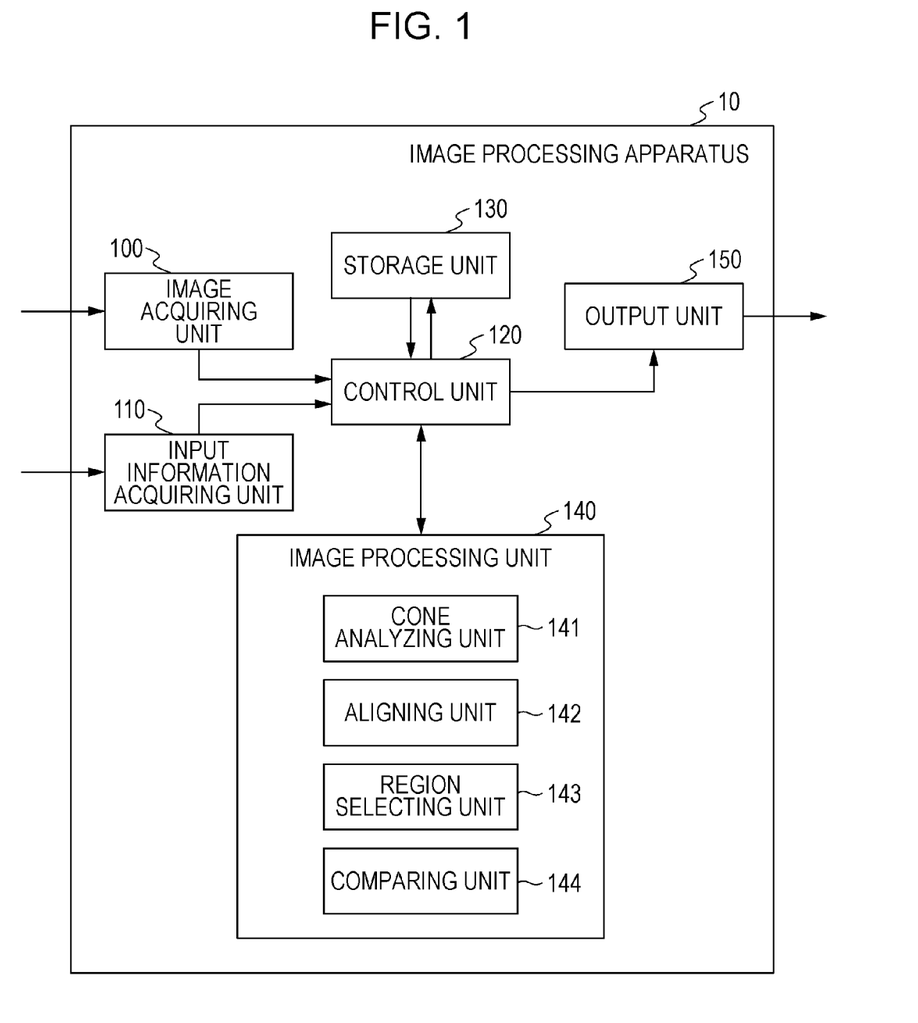
FIG. 1 illustrates an example of functionality configuration of an image processing apparatus according to an embodiment.

FIG. 1 illustrates a functionality configuration of an image processing apparatus 10 according to this embodiment.

Referring to FIG. 1, an image acquiring unit 100 acquires AO-SLO images acquired by an adaptive optical SLO apparatus. In other words, the image acquiring unit 100 corresponds to an example of a first acquiring unit configured to acquire a first eye fundus image of an eye to be examined on basis of return light from the eye to be examined having a corrected aberration of the eye to be examined. It further corresponds to an example of a second acquiring unit configured to acquire a second eye fundus image of the eye to be examined.

The acquired AO-SLO images are stored in a storage unit 130 under control of a control unit 120. An input information acquiring unit 110 is configured to acquire an input by a user. An image processing unit 140 includes a cone analyzing unit 141, an aligning unit 142, a region selecting unit 143, and a comparing unit 144. The image processing unit 140 performs a cone analysis on AO-SLO images captured at different times, aligns them and acquires an area where images are superimposed on each other. The cone analysis results are compared with respect to the region of interest selected from the superimposed area to assess a time-dependent change. An output unit 150 may not only output a calculated index or a comparison result to a monitor, for example, but also may output a processing result stored in the storage unit 130 to external storage such as a database, not illustrated.

Processing Steps of Image Processing Apparatus

Figure 2:
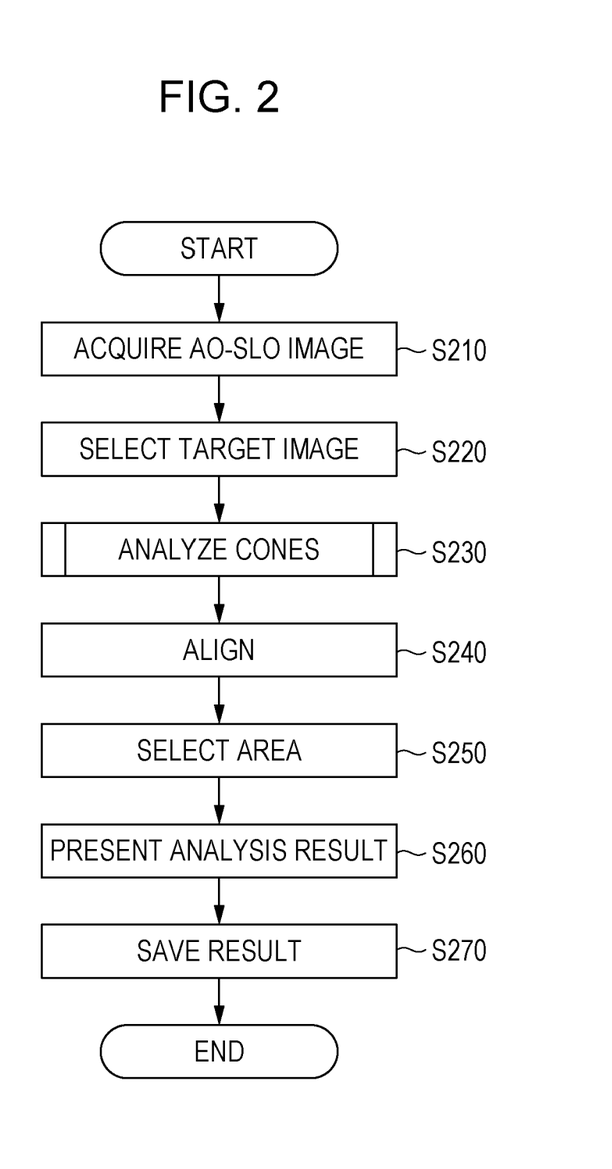
FIG. 2 is a flowchart describing an example of processing steps of the image processing apparatus according to the embodiment.

Next, processing step of the image processing apparatus 10 according to this embodiment will be described with reference to the flowchart in FIG. 2.

Step S210

In step S210, the image acquiring unit 100 acquires a plurality of wide fields SLO images (hereinafter called WF-SLO images) and AO-SLO images of the retina of an eye to be examined by using an adaptive optical SLO connected to the image processing apparatus 10.

Figure 3:
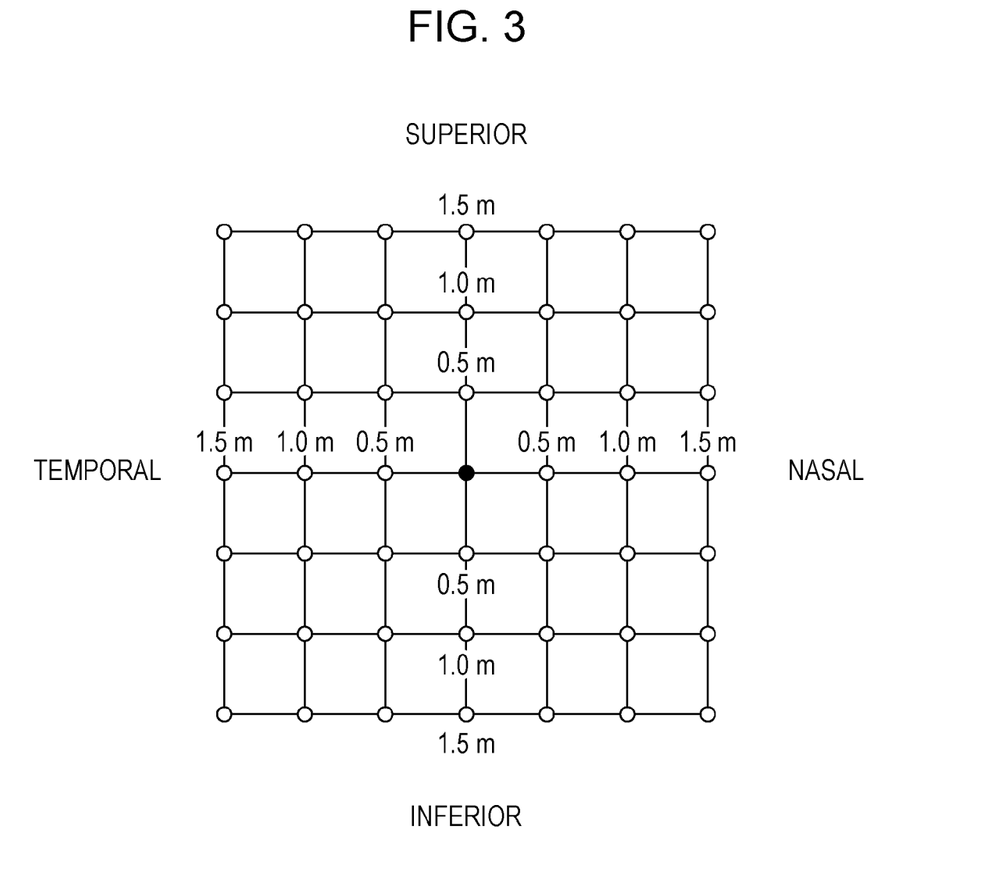
FIG. 3 is a schematic diagram illustrating an example of a fixation lamp map for operating a current position of a fixation lamp.

An exemplary imaging method is used here to perform a cone analysis on one eye to be examined. The aberration correction SLO apparatus used in this embodiment images an eye to be examined fixating on different positions with fixation lamps at different positions so that the retina at different positions may be imaged. FIG. 3 illustrates a fixation lamp map for operating a fixation lamp to be presented.

First, a fixation lamp is presented at a center selected on the fixation lamp map in FIG. 3. Hereinafter, the position will be called a reference position. In this case, imaging the eye to be examined fixing on the presented fixation lamp also allows imaging of a vicinity of a macula lutea. Under this state, a WF-SLO image and a plurality of AO-SLO images having different resolutions are captured. The WF-SLO image here refers to an image of the entire retina acquired by imaging a wide range of the retina for an image size of 8 mm×6 mm and a pixel size of 533×400. It should be noted that the image size and pixel size are not limited to those values but may have any other values, and the same applies hereinafter.

Mapping the AO-SLO images and the WF-SLO image may provide correspondences between narrow field AO-SLO images and the entire retina. The AO-SLO images here may be captured with three types of resolution for imaging area sizes of 1.7 mm×1.7 mm, 0.82 mm×0.82 mm, and 0.34 mm×0.34 mm and a common pixel size of 400×400. It should be noted that 3 or more types of resolution may be used, or two types of resolution may be used. Here, an AO-SLO image having an imaging area of 1.7 mm×1.7 mm will be called L image, an AO-SLO image having 0.82 mm×0.82 mm will be called an M image, and an AO-SLO image having 0.34 mm×0.34 mm will be called an S image. AO-SLO images may be captured for variable imaging periods of time and at variable frame rates. The AO-SLO images here include 64 images captured at a frame rate of 32 frames per second and for an imaging period of time of two seconds. It should be noted that the frame rate and the like may have any other values.

Next, the fixation position is moved by 0.5 mm in the Superior direction, and the eye is prompted to fixate on the fixation lamp at the moved position. Under this state, an M image and an S image are captured. In the same manner, the fixation position is moved by 0.5 mm in order in the Nasal direction, the Inferior direction, and in the Temporal direction, and corresponding M images and S images are captured.

Next, the fixation position is moved by 1.0 mm in the Superior direction, and the eye is prompted to fixate on the fixation lamp at the moved position. Under this state, an M image and an S image are captured. In the same manner, the fixation position is moved by 1.0 mm in order in the Nasal direction, the Inferior direction, and in the Temporal direction, and corresponding M images and S images are captured.

Figure 4:
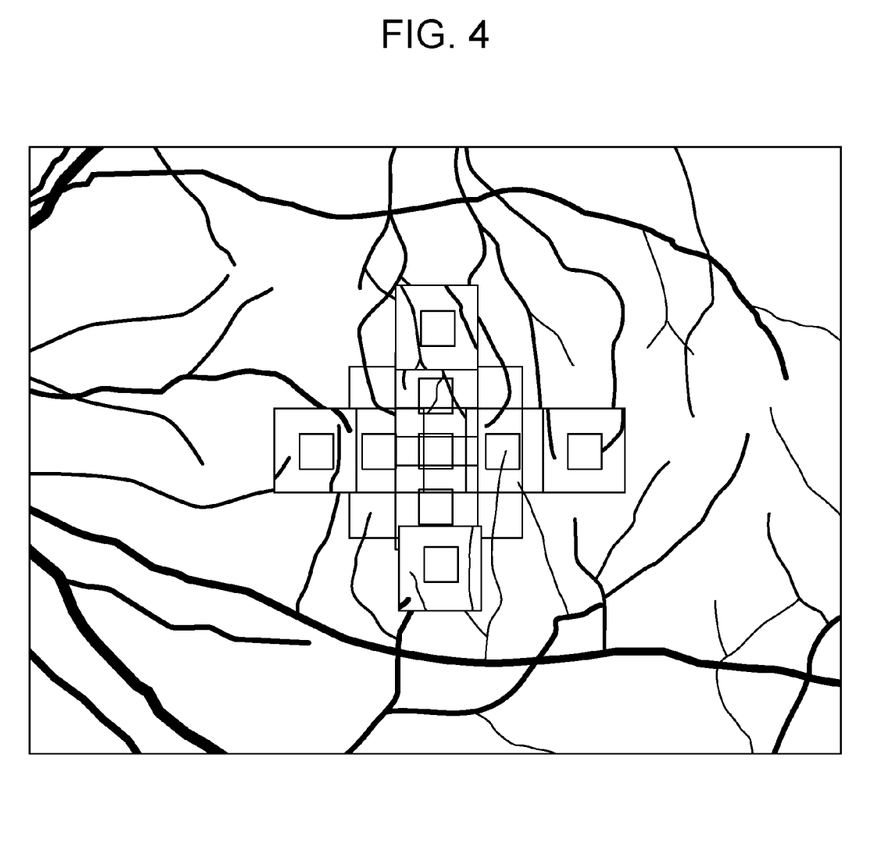
FIG. 4 illustrates examples of a captured WF-SLO image and AO-SLO image group.

FIG. 4 illustrates a schematic diagram of the thus captured WF-SLO image and AO-SLO image group of one eye to be examined. Referring to FIG. 4, the captured L, M, and S images are displayed over the WF-SLO image on basis of information on the corresponding fixation positions. As illustrated in FIG. 4, one WF-SLO image and 19 AO-SLO images (one L image, nine M images, and nine S images) will be handled as a reference set of one Study below. It should be noted that the reference set is not limited to the set described above.

Next, a Study of images captured at different times from the same eye to be examined is acquired from the Study.

The acquired WF-SLO image and AO-SLO image group of the eye to be examined are saved in the storage unit 130 under control of the control unit 120.

Step S220

Figure 5:
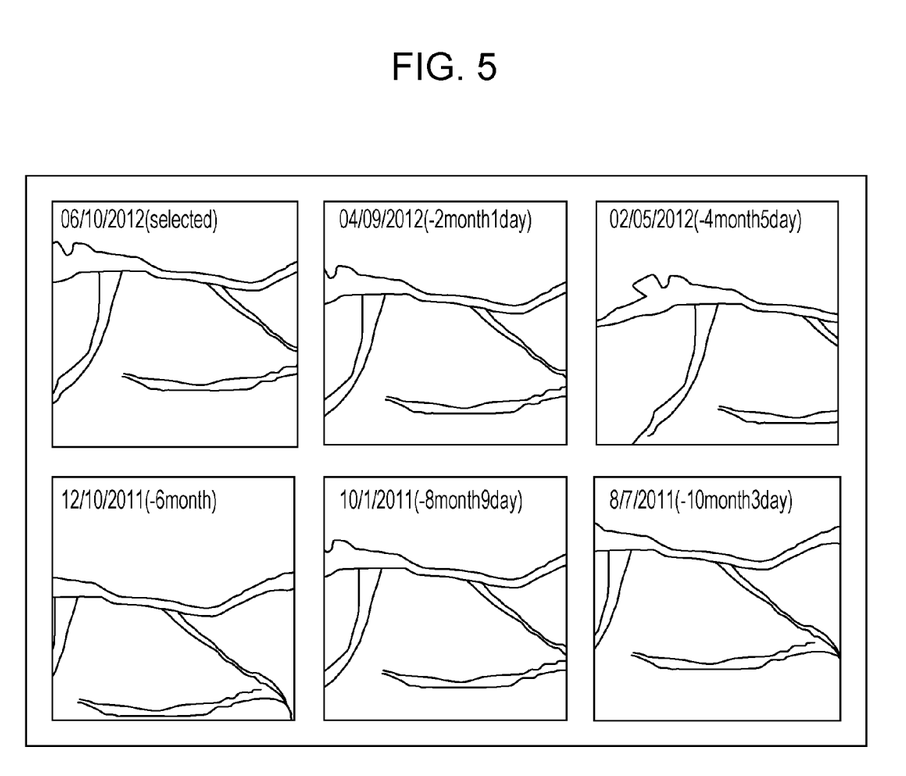
FIG. 5 illustrates an example of an AO-SLO image group to be presented for temporal comparison.

In step S220, the input information acquiring unit 110 acquires information on the AO-SLO image selected by a user from a plurality of Studies for the same eye to be examined saved in the storage unit 130. In this case, the information on the AO-SLO images may be a fixation position or a resolution. Here, the resolution corresponds to that of the S image. AO-SLO images included in another Study for the same eye to be examined, same fixation position, and same resolution as those of the selected AO- SLO image is acquired from the storage unit 130 and is saved in the storage unit 130 under control of the control unit 120 and also presented on a monitor, for example, through the output unit 150. FIG. 5 illustrates a schematic diagram showing a plurality of AO-SLO images presented on a monitor.

In FIG. 5, an AO-SLO image (selected image) captured lately is shown in the upper left part, and the other AO-SLO images are shown from there to the right direction and from the lower left part to the right direction in reverse chronological order. It should be noted that the arrangement of images on a monitor, for example, is not limited to the arrangement above but the images may be arranged arbitrarily. Each of the AO-SLO images shows its captured date and a difference from the captured date of the selected S image. A plurality of AO-SLO image group of the same eye to be examined, at the same fixation position and of the same resolution illustrated in FIG. 5 may sometimes be called serial assessment AO-SLO image groups.

Step S230

In step S230, the cone analyzing unit 141 performs a cone analysis on the serial assessment AO-SLO image groups saved in the storage unit 130 in step S220.

Figure 6:
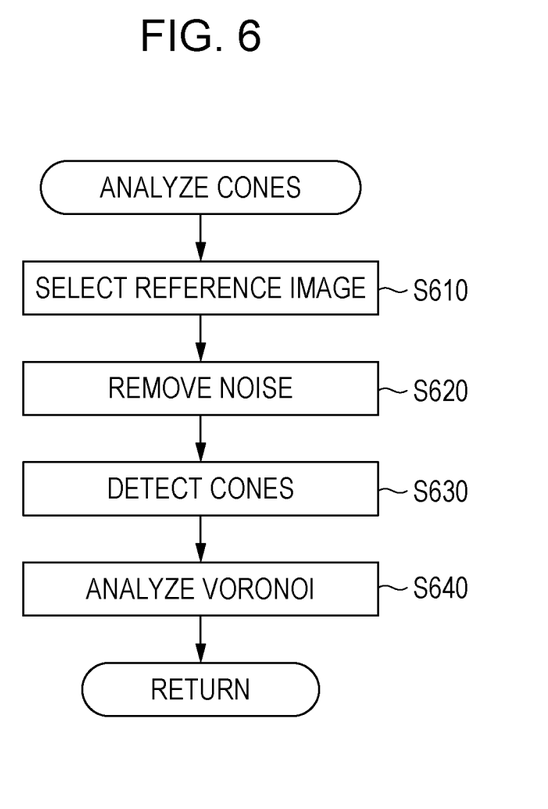
FIG. 6 is a flowchart describing details of an example of the cone analysis in FIG. 2.

FIG. 6 illustrates a flowchart describing details of a cone analysis on one AO-SLO image. For the cone analysis, all of serial assessment AO-SLO image groups undergo the following steps.

Step S610

In step S610, the input information acquiring unit 110 selects a reference frame from frames included in the AO-SLO images.

The AO-SLO images include 64 frames acquired by capturing one part for two seconds. However, because of a slight fixation movement of an eye to be examined, the imaged positions may differ among the 64 frames, and the frames may have a distortion. A frame captured well with less distortion is selected by a user as a reference frame from the 64 frames.

Having described that a reference frame is selected by a user, it may be selected in a software manner. For example, an average value or distribution of luminances may be calculated, and a frame having a highest average value or distribution may be selected. Alternatively, a reference frame may be selected which shows a ring structure indicative of the existence of cones through a frequency analysis.

The reference frame selected of the AO-SLO image is saved in the storage unit 130 under control of the control unit 120.

Step S620

In step S620, the cone analyzing unit 141 performs a preprocess to a cone analysis on basis of the reference frame of the AO-SLO image acquired in step S610. While various preprocesses may be performed, a noise reduction based on a frequency analysis is performed here. More specifically, a frequency conversion is performed on the reference frame, and an inverse conversion is performed thereon through a filter configured to remove a high frequency therefrom. Because it is known that the size of cone which tends to be the smallest (having the highest cone density) near a macula lutea is approximately 2 μm, the cutoff value for removing a frequency as noise may be 2 μm here. Vibrations having shorter cycles than 2 μm are removed as noise. It is further known that the cone density decreases as the distance from a macula lutea increases. Thus, the cutoff frequency may be changed on basis of the distance from macula lutea acquired from a fixation position used for imaging. For example, the cutoff frequencies may be defined on basis of distances from a macula lutea, such as 2 μm at the center of macula lutea, values increased by 1 μm for every distance of 0.5 mm from the macula lutea in the range from the center to a position at 1.0 mm from the center of macula lutea, and 4 μm (fixed) in the range from a position at 1.0 mm from the macula lutea.

Alternatively, the noise reduction may be performed by superimposing a plurality of frames acquired in AO-SLO images. More specifically, after 64 frames of each AO-SLO image undergo alignment processing such as an affine transform, and averaging processing is performed on an area corresponding to the reference frame. The accuracy of this method depends on the accuracy of the alignment processing. After the alignment processing is performed, processing of removing a high frequency component is performed through the frequency conversion above.

An image acquired in this manner will sometimes be called a preprocessed image.

Step S630

In step S630, the cone analyzing unit 141 performs cone detection on the preprocessed image acquired in step S620.

More specifically, a maximum value of the luminance of the preprocessed image may be detected. If the distance between points detected as a maximum value is larger than the size of cone known as common knowledge, it is determined as an influence of noise. Then, the detected points are merged for higher robustness of the detection. The size of cone applied here may be calculated on basis of a distance from a macula lutea to an AO-SLO image of interest, like step S620, for detection with higher accuracy.

A point having a value equal to or higher than a designated threshold value among the thus acquired detected points is determined as a cone. The threshold value may be a minimum luminance value of an image (where all detected points correspond to cones) or a luminance average value of an image.

Having described an example of the cone detection, a cone may be detected by various methods, without limiting to the foregoing. For example, pixels having a luminance value equal to or higher than a threshold value may only be selected, and a barycenter of the area in which the selected pixels are connected may be acquired. Alternatively, feature values of sub-areas may be calculated, and a cone may be detected therefrom by a pattern recognition method. More specifically, for example, Gabor feature value may be calculated from each of 11×11 pixel areas. Gabor feature vectors acquired from a plurality of sub-areas including detected points as cones at their centers and a plurality of sub-areas excluding such detected points may be used for learning by a support vector machine. A Gabor feature value is calculated for a new subject sub-area, and the learning result may be used to determine whether the center of the sub-area is a cone or not.

In addition to the detection by software, the correction may be performed manually by a user. In this case, the input information acquiring unit 111 acquires the position of the detected point corrected by a user from the detected points in step S630.

Step S640

In step S640, the cone analyzing unit 141 performs a Voronoi analysis on points detected in step S630.

More specifically, for all points detected in step S630, an area within the image is divided by a perpendicular bisector connecting detected points in vicinity to calculate Voronoi regions belonging to the detected points.

The results of the cone analysis are saved in the storage unit 130 under control of the control unit 120, and the processing then returns to step S230.

Step S240

In step S240, the aligning unit 142 aligns the serial assessment AO-SLO image groups saved in the storage unit 130 in step S220. In other words, the aligning unit 142 corresponds to an example of an aligning unit configured to align the first eye fundus image and the second eye fundus image. The alignment here uses the reference frame selected for the AO-SLO images in step S610.

More specifically, the "Selected" image which is referred for selecting a serial assessment AO-SLO image group and moving amounts of the other serial assessment AO-SLO image groups are calculated by phase only correlation method. It should be noted that the calculation of moving amounts may be performed by using the other methods than phase only correlation method.

Frequency conversion using FFT is performed on the reference frames of AO-SLO images to be compared. The phase only correlation function C(u,v) may be calculated by the following Equation (1):

$$C(u, v) = \frac{F(u, v)G(u, v)*}{|F(u, v)G(u, v)*|} \quad (1)$$

where the frequency-converted images above are F(u,v) and G(u,v).

The inverted FFT of C(u,v) may be acquired to detect a peak value and thus calculate the moving amounts. The calculated moving amounts are saved in the storage unit 130 under control of the control unit 120.

Figure 7:
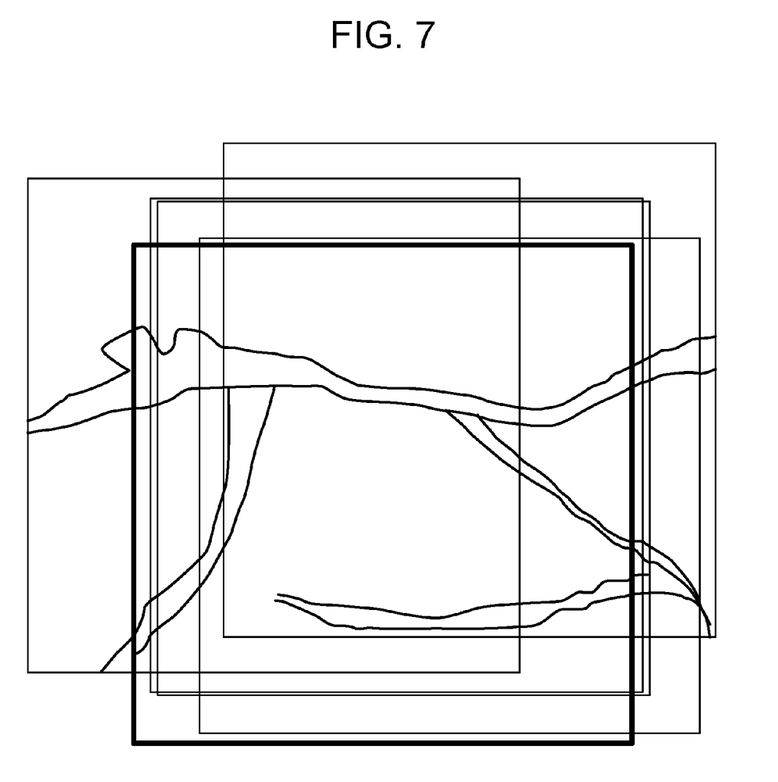
FIG. 7 illustrates an example of a superimposition of an AO-SLO image group for a serial assessment.

FIG. 7 illustrates an exemplary display on which serial assessment AO-SLO image groups are superimposed on basis of the calculated moving amounts. The display illustrated in FIG. 7 will be called a superimposed display of serial assessment AO-SLO image groups. FIG. 7 shows the frame of the Selected image only by using a thick line.

Having described here an example of a method of alignment by software, the positions may be aligned manually. More specifically, the positions of AO-SLO images may be moved by click & drag with a mouse with reference to a characteristic of a blood vessel, for example. They may be aligned only manually. Alternatively, they may be aligned by software as described above and then may be corrected manually. Having described above that the alignment is performed by using the reference frame selected in step S610, a combination frame created from frames of an AO-SLO image may be used. An example of the combination frame creation method is disclosed in "Retinal motion estimation in adaptive optics scanning laser ophthalmoscopy" Curtis R. Vogel et al. Optics Express, vol. 14, issue 2, 487-497 (2006). Further alternatively, a preprocessed image acquired in step S620 may be used for the alignment.

Step S250

In step S250, the region selecting unit 143 selects a region of interest on basis of the alignment result of the serial assessment AO-SLO image groups acquired in step S240. In other words, the region selecting unit 143 corresponds to an example of a region setting unit configured to set a candidate region of interest on basis of the alignment.

The term "region of interest" here refers to a region for calculating an index for assessment of a change due to an advancement of a disease through temporal comparison of the cone analysis results acquired in step S230. In order to compare all serial assessment AO-SLO image groups, a region included in all of the serial assessment AO-SLO image groups is acquired. Examples of the index may include the number of detected points acquired in step S630, the density acquired by dividing the number of detected points by the area of the region, the distance to the nearest detected point acquired in step S640, and the proportion that the Voronoi region is a hexagon.

Figure 8A:
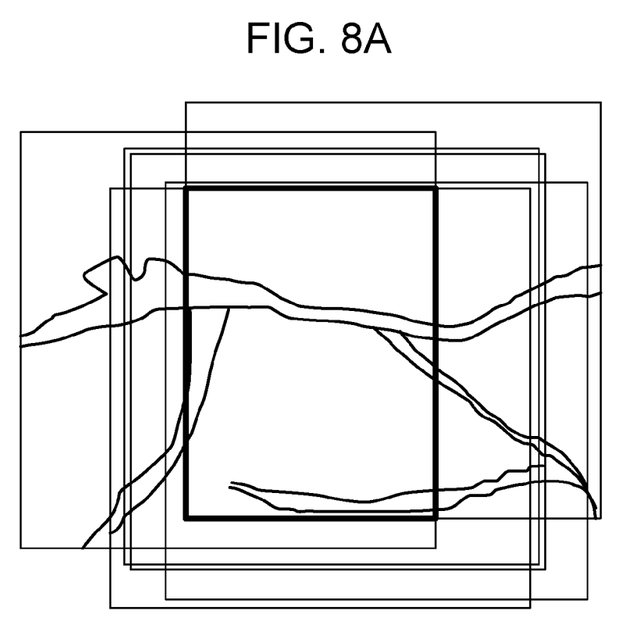
FIGS. 8A and 8B illustrate an example of a superimposition based on the number of superimposed images.
Figure 8B:
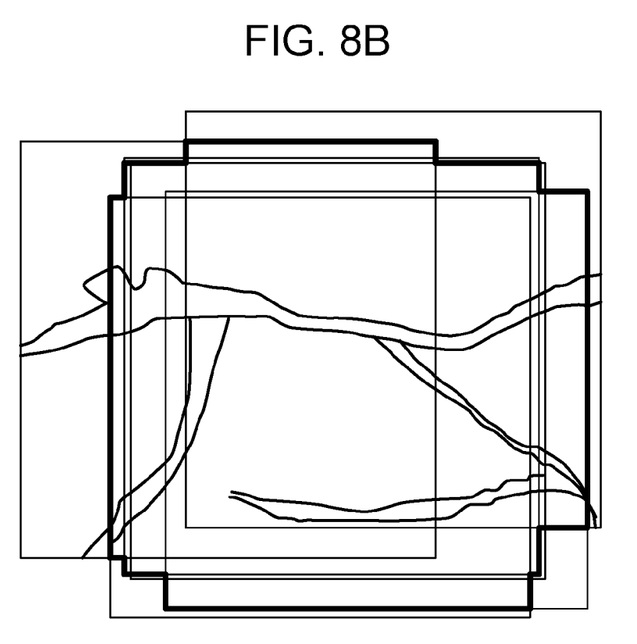

FIG. 8A illustrates a diagram having a thick line frame area where all serial assessment AO-SLO image groups are superimposed based on the alignment result acquired in FIG. 7. In other words, all eye fundus images are superimposed as a result of the alignment in the thick line frame area. It should be noted that the thick line frame area is a selectable maximum area for comparing all serial assessment AO-SLO image groups and is therefore a minimum area of the candidate region of interest. FIG. 8B illustrates a diagram having a thick line frame area where at least two serial assessment AO-SLO images are superimposed for comparison. In other words, referring to FIG. 8B, the region which is a candidate region of interest where at least two eye fundus images are superimposed as a result of the alignment is a maximum area of the candidate region of interest. The region may be shown in a color based on the number of serial assessment AO-SLO images superimposed in FIG. 8B. Thus, several serial assessment AO-SLO image groups may be compared in order to select the region of interest including a characteristic object if any.

As illustrated in FIGS. 8A and 8B, a candidate region of interest may be identified and presented in accordance with the number of eye fundus image superimposed as a result of the alignment.

Figure 9A:
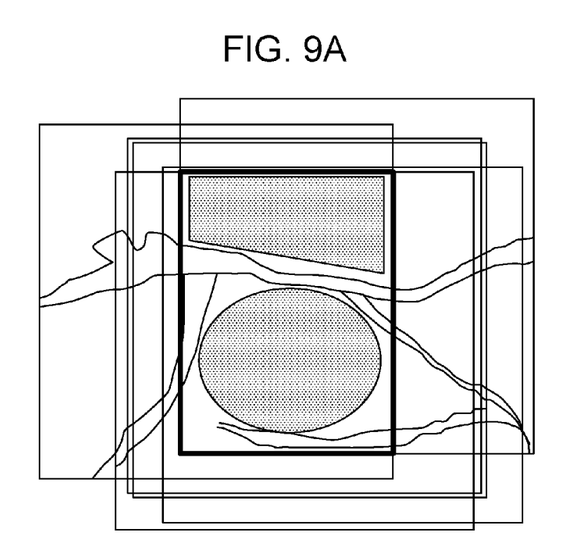
FIGS. 9A and 9B illustrate examples of region selections.
Figure 9B:
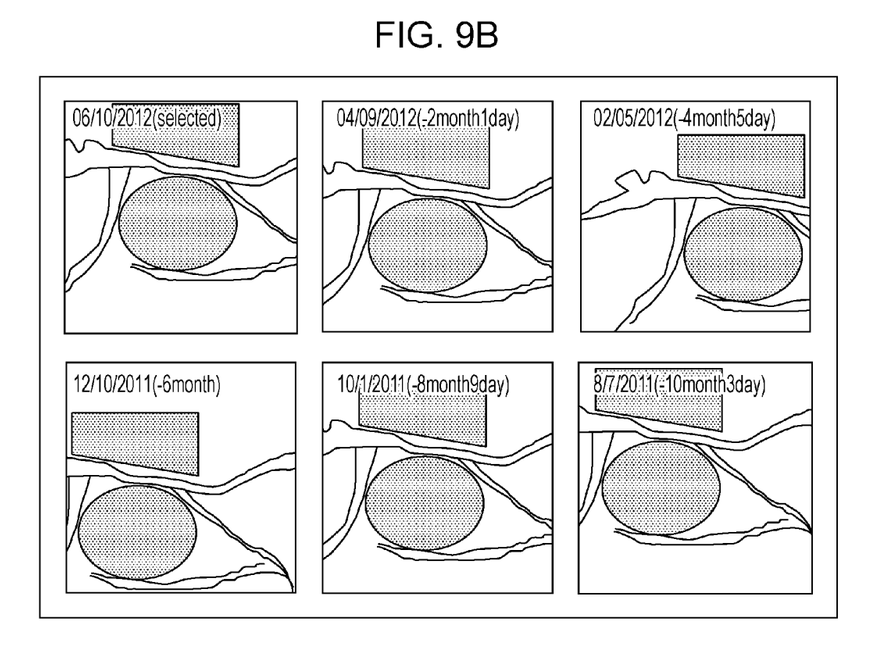

A user may select a region of interest from a selected region in the thick line frame area. FIGS. 9A and 9B illustrate examples of regions selected by a user. FIG. 9A illustrates a selected region shown on a superimposed display of serial assessment AO-SLO image groups, and FIG. 9B illustrates a selected region on individual AO-SLO images. It should be noted that the displays illustrated in FIGS. 9A and 9B may be shown simultaneously on a display unit under control of a display control unit or may be switched in response to an instruction from a user. In FIG. 9A, a region is selected in an area where all serial assessment AO-SLO image groups are superimposed. A rectangle, a polygon, or an ellipse, for example may be available for the form of the selected region, which may be set by clicking with a mouse by a user. When a blood vessel is included in those images, the luminance under the blood vessel is lower, which may also lower the visual-cell detection accuracy. The region selection is performed by avoiding a blood vessel. In other words, a region of interest is selected from an area excluding a blood vessel area. It should be noted that it may be configured to allow automatic recognition of a blood vessel area and disable a user to select such the recognized blood vessel area. Referring to FIG. 9B, against a case with insufficient accuracy of the alignment, a user may correct the position of a selected region on each of the images. In this case, the selected region may be moved by click & drag with a mouse without changing its size and shape. It should be noted that the reference set illustrated in FIG. 4 may be displayed as well as the display in FIG. 9B on a display unit. The AO-SLO image without the WF-SLO image in FIG. 4 may be displayed along with the displays in FIG. 9B and FIG. 4.

Figure 10A:
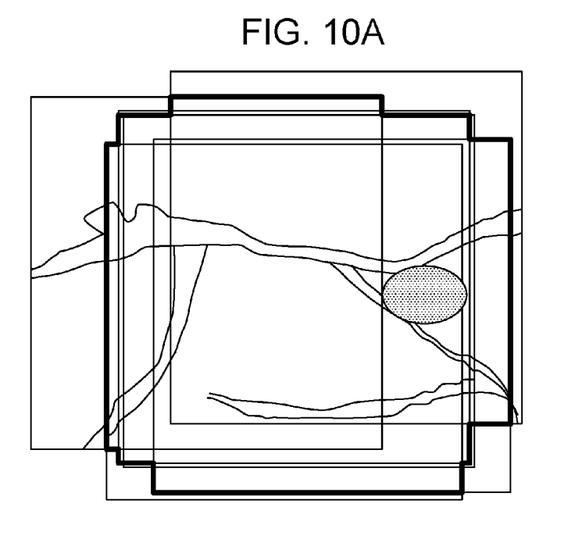
FIGS. 10A and 10B illustrate an example of a clearly shown AO-SLO image group for a serial assessment that is to be a comparison subject after the region selection operation.
Figure 10B:
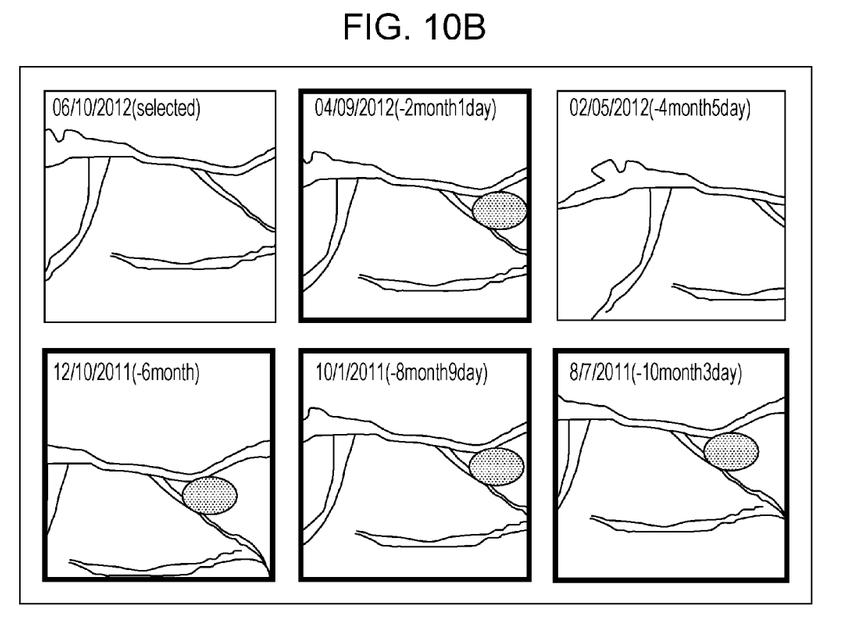

While FIG. 8B illustrates the display indicating the number of superimposed serial assessment AO-SLO images, serial assessment AO-SLO images superimposed at a position pointed with a mouse in FIG. 10A are illustrated in FIG. 10B. AO-SLO images including a selected region of interest are indicated on FIG. 10B. In other words, eye fundus images to be compared including a selected region of interest are identified and presented from candidate region of interests. This allows selection of a region of interest by checking the number and captured times of AO-SLO images to be compared.

A result of the region selection is saved in the storage unit 130 under control of the control unit 120.

Step S260

In step S260, the comparing unit 144 compares serial assessment AO-SLO image groups acquired in step S220 on basis of the analysis results performed in steps S230 to S250.

Figure 11:
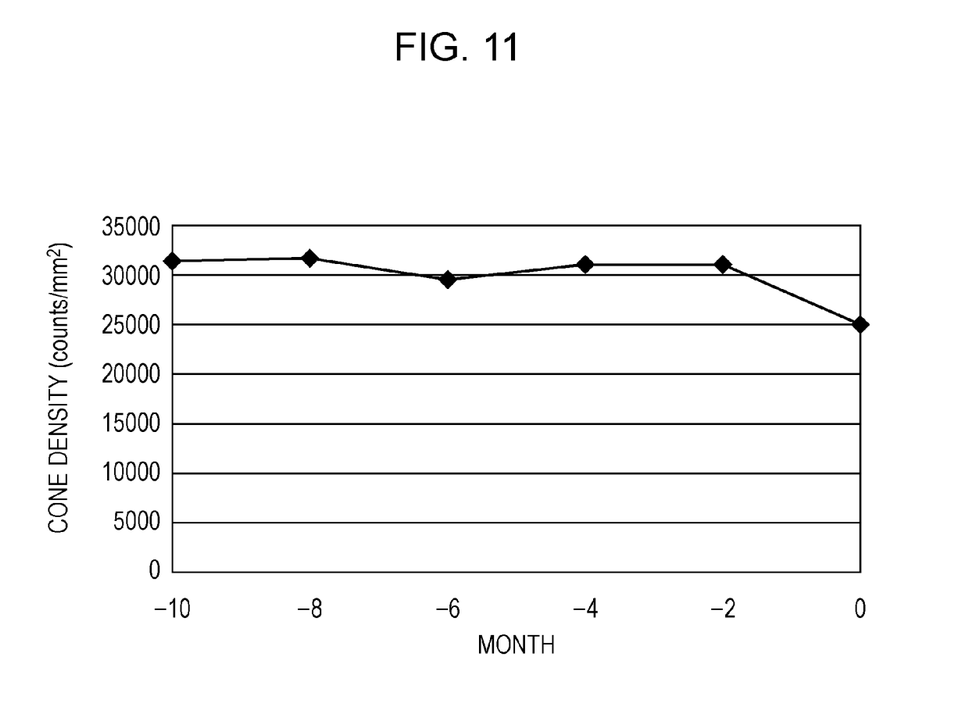
FIG. 11 illustrates an exemplary graph illustrating time-dependent changes of the cone density.

FIG. 11 illustrates an exemplary graph showing time-dependent changes of cone density measured in the selected region in FIGS. 9A and 9B. The indices acquired as a result of a cone analysis in step S230 are to be compared and more specifically may be the number of cones, the density acquired by dividing the number of cones by the area of the region, the distance to the nearest cone, the area of the Voronoi region, or the proportion that the Voronoi region is a hexagon, without limiting to the foregoing.

Step S270

In step S270, the control unit 120 saves in a database processing results stored in the storage unit 130 such as the calculated indices and comparison results.

The aforementioned configuration allows a temporal change assessment on an identical region of an eye fundus based on results of analysis of a plurality of AO-SLO images acquired over time by an adaptive optical SLO apparatus.

The aforementioned configuration allows selection of a region of interest for analysis and comparison on a plurality of AO-SLO images acquired over time by an adaptive optical SLO apparatus in consideration of the number of AO-SLO images to be compared and their captured times.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-287254, filed Dec. 28, 2012, which is hereby incorporated by reference herein in its entirety.

What is claimed is:

1. An ophthalmological apparatus comprising:
   a first acquiring unit configured to acquire a first AO-SLO (Adaptive Optics Scanning Laser Ophthalmoscope) image of an eye to be examined;
   a second acquiring unit configured to acquire a second AO-SLO image of the eye to be examined, wherein the first AO-SLO image and the second AO-SLO image are captured at different times and at a same fixation position, and a resolution of the first AO-SLO image is the same as a resolution of the second AO-SLO image;
   an aligning unit configured to align the first AO-SLO image and the second AO-SLO image;
   a display control unit configured to cause a display unit to display the first AO-SLO image and the second AO-SLO image in a superimposed manner based on an alignment result of the alignment unit; and
   a region setting unit configured to set a region of interest based on a user selection to a displayed area where the first AO-SLO image and the second AO-SLO image are superimposed,
   wherein the display control unit causes the display unit to display information regarding time-dependent changes of a visual cell based on a visual cell acquired from the region of interest in the first AO-SLO image and a visual cell acquired from the region of interest in the second AO-SLO image.

2. The ophthalmological apparatus according to claim 1 wherein the region setting unit prohibits a user selection of a blood vessel region.

3. A method of controlling an ophthalmological apparatus for imaging a fundus of an eye, the method comprising:
   a first acquiring step to acquire a first AO-SLO (Adaptive Optics Scanning Laser Ophthalmoscope) image of an eye to be examined;
   a second acquiring step to acquire a second AO-SLO image of the eye to be examined, wherein the first AO-SLO image and the second AO-SLO image are captured at different times and at a same fixation position, and a resolution of the first AO-SLO image is the same as a resolution of the second AO-SLO image;
   an aligning step to align the first AO-SLO image and the second OA-SLO image;
   a display control step to cause a display unit to display the first AO-SLO image and the second AO-SLO image in a superimposed manner based on an alignment result of the aligning step; and
   a region setting step to set a region of interest based on a user selection to a displayed area where the first AO-SLO image and the second AO-SLO image are superimposed,
   wherein, in the display control step, the display unit displays information regarding time-dependent changes of a visual cell based on a visual cell acquired from the region of interest in the first AO-SLO image and a visual cell acquired from the region of interest in the second AO-SLO image.

4. A non-transitory storage medium configured to store a program to cause a computer to perform the method according to claim 3.

5. The ophthalmological apparatus according to claim 1, wherein the information regarding time-dependent changes of a visual cell is information regarding time-dependent changes of visual cell density.

6. The ophthalmological apparatus according to claim 5, wherein the information regarding time-dependent changes of visual cell density is a graph showing time-dependent changes of visual cell density.

7. The ophthalmological apparatus according to claim 1, wherein the information regarding time-dependent changes of a visual cell is information regarding time-dependent changes of the number of visual cells.

8. The ophthalmological apparatus according to claim 1, wherein the display control unit emphasizes the displayed area where the first AO-SLO image and the second AO-SLO image are superimposed.

9. The ophthalmological apparatus according to claim 1, wherein the display control unit causes the display unit to simultaneously display the first AO-SLO image and the second AO-SLO image side by side, the first AO-SLO image and the second AO-SLO image not being superimposed each other, and wherein the display control unit causes the display unit to display the region of interest on the first AO-SLO image and the second AO-SLO image respectively.

10. The ophthalmological apparatus according to claim 9, wherein the display control unit causes the display unit to display a difference between time of capturing the first AO-SLO image and time of capturing the second AO-SLO image.

11. The ophthalmological apparatus according to claim 1, wherein the user selection is performed with use of a computer mouse.

12. The ophthalmological apparatus according to claim 1, wherein the display control unit causes the display unit to simultaneously display the first AO-SLO image and the second AO-SLO image side by side, the first AO-SLO image and the second AO-SLO image not being superimposed each other, and wherein the display control unit causes the display unit to display the region of interest on the first AO-SLO image and the second AO-SLO image respectively, and wherein the display control unit causes the display unit to change display modes between a first mode that the first AO-SLO image and the second AO-SLO image are superimposed and a second mode that the first AO-SLO image and the second AO-SLO image are not superimposed.

13. An ophthalmological apparatus comprising:

a first acquiring unit configured to acquire a first AO-SLO (Adaptive Optics Scanning Laser Ophthalmoscope) image of an eye to be examined;

a second acquiring unit configured to acquire a second AO-SLO image of the eye to be examined, wherein the first AO-SLO image and the second AO-SLO image are captured at different time and at a same fixation position, wherein a resolution of the first AO-SLO image is same as a resolution of the second AO-SLO image;

an aligning unit configured to align the first AO-SLO image and the second AO-SLO image; and a display control unit configured to cause a display unit to display the first AO-SLO image and the second AO-SLO image in a superimposed manner based on the alignment;

wherein the display control unit emphasizes the displayed area where the first AO-SLO image and the second AO-SLO image are superimposed.

* * * * *